US010780028B2

(12) United States Patent
Sheirs

(10) Patent No.: US 10,780,028 B2
(45) Date of Patent: Sep. 22, 2020

(54) PERSONAL CARE CLEANING PRODUCT IN TABLET FORM

(71) Applicant: Kegel, LLC, Lake Wales, FL (US)

(72) Inventor: Dennis W. Sheirs, Las Vegas, NV (US)

(73) Assignee: Kegel, LLC, Lake Wales, FL (US)

( * ) Notice: Subject to any disclaimer, the term of this patent is extended or adjusted under 35 U.S.C. 154(b) by 0 days.

(21) Appl. No.: 16/251,163

(22) Filed: Jan. 18, 2019

(65) Prior Publication Data

US 2019/0282837 A1    Sep. 19, 2019

Related U.S. Application Data

(60) Provisional application No. 62/620,919, filed on Jan. 23, 2018.

(51) Int. Cl.

| | |
|---|---|
| *A61K 8/02* | (2006.01) |
| *A61K 8/34* | (2006.01) |
| *A61K 8/73* | (2006.01) |
| *A61K 8/365* | (2006.01) |
| *A61K 8/19* | (2006.01) |
| *A61Q 19/10* | (2006.01) |
| *C11D 17/00* | (2006.01) |
| *C11D 3/22* | (2006.01) |
| *A61Q 5/02* | (2006.01) |

(52) U.S. Cl.
CPC .............. *A61K 8/0216* (2013.01); *A61K 8/02* (2013.01); *A61K 8/0204* (2013.01); *A61K 8/19* (2013.01); *A61K 8/34* (2013.01); *A61K 8/345* (2013.01); *A61K 8/365* (2013.01); *A61K 8/732* (2013.01); *A61Q 19/10* (2013.01); *C11D 3/222* (2013.01); *C11D 17/0047* (2013.01); *C11D 17/0073* (2013.01); *A61Q 5/02* (2013.01)

(58) Field of Classification Search
None
See application file for complete search history.

(56) References Cited

U.S. PATENT DOCUMENTS

| | | | | |
|---|---|---|---|---|
| 2,560,097 | A * | 7/1951 | Emerson, Jr. .......... | C11D 3/382 510/138 |
| 3,318,817 | A | 5/1967 | Smith | |
| 6,147,120 | A * | 11/2000 | Swart ..................... | A61K 8/347 514/482 |
| 7,326,674 | B2 | 2/2008 | Sheirs et al. | |
| 2010/0222246 | A1 * | 9/2010 | Doi ......................... | A61K 8/39 510/121 |
| 2014/0294818 | A1 * | 10/2014 | Chen ...................... | A61K 45/06 424/133.1 |
| 2014/0308216 | A1 | 10/2014 | Commell et al. | |
| 2015/0272124 | A1 * | 10/2015 | Pedersen ................ | A61K 8/602 514/635 |
| 2015/0328127 | A1 * | 11/2015 | Chen ....................... | A61K 8/86 510/136 |
| 2016/0362634 | A1 * | 12/2016 | Kielbania, Jr. ........ | C11D 1/835 |
| 2017/0107457 | A1 * | 4/2017 | Gori ...................... | C11D 3/38636 |
| 2019/0024023 | A1 * | 1/2019 | Omont-Manteghetti ..................... | C11D 3/3955 |
| 2019/0070086 | A1 * | 3/2019 | Cetti ....................... | A61K 8/445 |

FOREIGN PATENT DOCUMENTS

| | | |
|---|---|---|
| CN | 107510747 | 12/2017 |
| KR | 20170009164 A * | 1/2017 |
| WO | WO2004100817 A2 | 11/2004 |
| WO | WO201400001092 A1 | 1/2014 |

OTHER PUBLICATIONS

Product information sheet for alkyl aryl sodium sulfonate, obtained from the webpage http://www.chemicalland21.com/specialtychem/perchem/ALKYL%20ARYL%20SODIUM%20SULFONATE.htm (date unavailable).*
Product information sheet for sodium sulfate, obtained from the webpage https://www.sigmaaldrich.com/catalog/product/sigald/238597?lang=en&region=US (date unavailable).*
Petty, "The "How's" & Why's of Homemade DIY Natural Cleaning Products" (Internet article obtained from Google Search) (Year: 2019).*
Machine-assisted English translation for KR 2017-0009164 (Year: 2017).*
ISA-KR, "Notification of Transmittal of the International Search Report and the Written Opinion of the International Searching Authority, or the Declaration", PCT International Patent Application No. PCT/US19/014267, dated Jun. 3, 2019, 14 pages.
Puri et al., "Formulation and evaluation of diclofenac sodium tablet using isolated starch from unripe papaya fruits as disintegrants", Indo American Journal of Pharmaceutical Research, 2013, No. 3, pp. 9183-9189.
Cosmetic Science Talk, "Quick Dissolve Soap Tablets", Mar. 2015, 2 pages.
the chemistry store.com, "Making Your Bath Bombs Foam", at least as early as Sep. 22, 2017, 2 pages.

* cited by examiner

*Primary Examiner* — Sin J Lee
(74) *Attorney, Agent, or Firm* — Walter W. Duft

(57) ABSTRACT

In one aspect, a personal care cleaning composition in tablet form may include a surfactant and a starch composition formed from starch, alcohol and water. The tablet may be formed using a method that includes preparing the starch slurry composition comprising the starch, alcohol and water, preparing a mixture of the starch slurry composition and the surfactant, and pressing the mixture into tablet form. In another aspect, a personal care cleaning composition in tablet form may include a surfactant, a starch composition formed from starch, alcohol and water, sodium carbonate, sodium bicarbonate, citric acid, and glycol ether. The tablet may be formed using a method that includes preparing the starch slurry composition comprising the starch, alcohol and water, preparing a mixture of the starch slurry composition and the surfactant, the sodium carbonate, the sodium bicarbonate, the citric acid and the glycol ether, and pressing the mixture into tablet form.

30 Claims, No Drawings

PERSONAL CARE CLEANING PRODUCT IN TABLET FORM

BACKGROUND

1. Field of the Disclosure

The present disclosure relates to personal care products, and more particularly to products for personal cleaning.

2. Description of the Prior Art

By way of background, personal cleaning products have a long history. Soap bars have for many years been the primary washing method for hands, body and hair. Although soap bars are still used, liquids have recently become the dominant form. Liquid soap offers cleaning product formulators the flexibility to create products for specific uses, such as hand cleaners, facial soaps, body washes and hair shampoos.

Both solid and liquid form soap products are designed to be used multiple times. A disadvantage of solid form products is that they tend to become slimy and dirty over time. A disadvantage of liquid form products is that they require plastic packaging, which increases manufacturing cost and shipping weight, and is environmentally unfriendly. Liquid form products also tend to be bulkier than solid form products, and may not be as convenient as solid form products for travelers or in rural areas. Solid form products may be superior from this standpoint, but they do not store well after initial use and do not offer the benefits of liquid formulations.

It is to improvements in the field of personal care cleaning products that the present disclosure is directed.

SUMMARY

Disclosed herein are compositions and methods for producing personal care cleaning products in tablet form. The tablets have the ability to dissolve rapidly in water of any temperature, and are very portable, easy to ship, and convenient to use.

In one aspect, a personal care cleaning composition in tablet form may include a surfactant and a starch composition formed from starch, alcohol and water. The tablet may be created using a method that includes preparing the starch composition as a slurry, mixing the starch slurry with the surfactant, and pressing the mixture into tablet form.

In another aspect, a personal care cleaning composition in tablet form may include a surfactant, a starch composition formed from starch, alcohol and water, sodium carbonate, sodium bicarbonate, citric acid, and glycol ether. The tablet may be created using a method that includes preparing the starch composition as a slurry, preparing a mixture of the starch slurry and the surfactant, the sodium carbonate, the sodium bicarbonate, the citric acid and the glycol ether, and pressing the mixture into tablet form.

DETAILED DESCRIPTION OF EXAMPLE EMBODIMENTS

As noted by way of background above, traditional solid form and liquid form personal care cleaning products have a number of disadvantages. The personal care cleaning products disclosed herein, being in tablet form, overcome these problems. The cleaning tablets are easy to transport, and do not require expensive bulky packaging. The tablets are made in a way that allows water to penetrate quickly and break apart the tablet, typically in less than a minute. Water temperature is not a factor in the dissolve time, thus rendering the tablets easy to use anywhere there is water. If desired, the tablet formulas can be adjusted to work as a hand wash, a face wash, a body wash, or a hair wash. The tablets can be used directly on the body, like a soap bar, or they can be dissolved in a small amount of water prior to use.

In an embodiment, the tablets may incorporate liquid and solid materials to obtain to the final form. In an embodiment, a unique starch slurry composition may be used to provide rapid dissolve time and allow for good compressibility of the tablet. In an embodiment, binding of the tablet may be assisted by a chemical from the glycol ether family in combination with the other materials of the tablet. Both effervescent and non-effervescent tablets may be produced. The tablets may contain sulfates or they may be sulfate-free.

Example effervescent tablets may be formed from a surfactant that is sulfate-containing or sulfate-free, a starch composition comprising starch, alcohol and water, together with additional ingredients such as sodium carbonate, sodium bicarbonate, citric acid and glycol ether. Example non-effervescent tablets may be formed from a surfactant that is sulfate-containing or sulfate-free, and a starch composition comprising starch, alcohol and water.

In an embodiment, the surfactant may be powder-based or in liquid form. As previously noted, the surfactant may be sulfate-containing or it may be substantially sulfate free. Any number of different surfactants may be used, either alone or in combination, including non-ionic surfactants and ionic surfactants (e.g., anionic, cationic, zwitterionic). In example tablet formulas described in more detail below (see Tables 3, 4, 5 and 6), the surfactant is selected from the group consisting of sodium lauroyl oat amino acids, silicone emulsions, sodium laureth sulfate, lauryl glucoside, cocamidopropyl betaine, sodium lauryl sulftate, sodium cocoyl isethionate, sodium sulfocuccinate and n-methyl glycine. Other surfactants that have been used in successfully tested tablet compositions include polydimethylsiloxane and alkyl glycoside.

In an embodiment, the starch composition may be provided as a slurry comprising starch, alcohol and water. The starch slurry composition functions as an excellent excipient for enhancing tablet solubility. Various starch slurry compositions were made and tested in an attempt to optimize the desired characteristics of minimizing disruption of tablet binding and decreasing tablet dissolve time. Testing revealed that (un-modified) corn starch provides superior results when compared to other native starches. Native corn starch was likewise found be superior to modified starches, such as maltodextrin and gelatinized corn starch. Various types of cellulose were also tested. These included carboxy methyl cellulose, hydroxy propyl methyl cellulose, and croscarmellose sodium. All of the cellulose materials presented various problems due to the tablets being too hard or producing poor binding of materials. Other variations of cellulose type materials were also tested and created similar problems.

Through a process of experimentation, it was determined that an embodiment in which the starch slurry composition comprised water and corn starch modified with OH groups provided the best combination of feel, binding, and ability to allow water to push the tablet apart quickly. In this embodiment, isopropyl alcohol was used to provide the OH groups. The OH-modified corn starch/water slurry of this embodiment performed better than either a mixture of dried corn starch and water, and just plain corn starch. The starch slurry composition of this embodiment also out-performed similar mixtures of starch, isopropyl alcohol and water that swapped out the corn starch in favor of other native starches (e.g., potato, rice or wheat starch), modified starches or cellulose. The tested dissolve times for corn starch, isopropyl alcohol and water mixtures were consistently twice as fast as other starch mixtures containing water, isopropyl alcohol and a substitute for corn starch. The tested dissolve times (until about 100% dissolved) were 1 minute on average for corn starch/isopropyl alcohol/water mixtures as compared to 2.5 minutes on average for the non-corn starch mixtures. The starch mixtures containing corn starch, alcohol and water also dissolved twice as quickly as similar mixtures containing corn starch and water, but no alcohol.

The glycol ether may be selected from the group consisting of ethylene oxide glycol ethers and propylene oxide glycol ethers. More particularly, the glycol ether may be selected from the group consisting of ethylene glycol phenyl ether, ethylene glycol butyl ether, dipropylene glycol n-butyl ether, dipropylene glycol methyl ether, tripopylene glycol methyl ether, and polyethylene glycol 800 MW or higher.

The glycol ether was discovered to function as an excellent tablet binder. For purposes of comparison, several other tablet binders were tested. These included lactose, starches, sugars, calcium, phosphate, and cellulose. The listed materials created tablets that were deemed to be too hard for purposes of a personal care cleaning product.

For effervescent tablets, glycol ethers react with citric acid to form a liquid precipitate that is tacky and gummy. The tablets were pressed under low pressure (2-4 tons), and were observed to became harder following tablet formation due to the internal reaction of the glycol ether and the citric acid. The glycol ether coalesced well with water, allowing for a more porous tablet for quicker water penetration during use. Sodium sulfosuccinate was used as a surfactant in these tablets, and was observed to become part of the binder mixture and to allow water to wet through more quickly. The final bound mixtures were observed to have a long shelf life with good feel when used directly in the hands.

Effervescent Cleaning Tablet Preparation

In an embodiment, the following example formula may be used to produce a personal care cleaning composition that can be formed into effervescent cleaning tablets:

(a) Starch slurry composition at about 1-50% by weight, with about 35-45% by weight being preferred;
(b) Sodium carbonate (soda ash) at about 1-30% by weight, with about 16-30% by weight being preferred;
(c) Surfactants at about 1-10% by weight, with about 4-10% by weight being preferred;
(d) Sodium bicarbonate at about 1-20% by weight, with about 10% by weight being preferred;
(e) Citric acid at about 1-30% by weight, with about 21-22% by weight being preferred; and
(f) Glycol ether at about 0.25-0.75% by weight, with about 0.3-0.7% by weight being preferred.

Table 1 below summarizes the above-described formula for effervescent tablets. All percentages are by weight.

TABLE 1

Example Formula for Effervescent Tablets

| INGREDIENT | % BY WEIGHT | |
|---|---|---|
| | BROAD RANGE | PREFERRED RANGE |
| Starch Slurry Composition | ~1-50% | ~35-45% |
| Sodium Carbonate | ~1-30% | ~16-30% |

TABLE 1-continued

Example Formula for Effervescent Tablets

| INGREDIENT | % BY WEIGHT | |
|---|---|---|
| | BROAD RANGE | PREFERRED RANGE |
| Surfactant(s) | ~1-10% | ~4-10% |
| Sodium Bicarbonate | ~1-20% | ~10% |
| Citric Acid | ~1-30% | ~21-22% |
| Glycol Ether | ~0.25-0.75% | ~0.3-0.7% |

The effervescent tablet compositions of Table 1 can be made using a three-stage process. A first stage of involves preparing a starch slurry composition as described hereinafter in connection with Table 2 (see below). A second stage involves preparing a premix that includes the sodium carbonate, the glycol ether, and one or more surfactants of Table 1 that may be in liquid form. The one or more premix surfactants may be sulfate-free, thereby allowing the premix to be used in final compositions that are either sulfate-containing or sulfate-free. Example sulfate-free premix formulas are described in more detail hereinafter in connection with Table 3. A third stage involves combining the starch slurry composition and the premix with the remaining ingredients of Table 1, namely, the sodium bicarbonate and the citric acid of Table 1, together with one or more additional surfactants of Table 1 that may be in powder form. The one or more additional surfactants may either be sulfate-containing or sulfate free, depending on the desired final tablet composition. It should be noted that the first and second stages of effervescent tablet formulation need not be performed in any particular order. The first stage could be performed prior to the second stage, or visa versa.

The rationale for using the above-described three-stage tablet formulation process is to isolate the water of the starch slurry composition from the effervescent reaction, and to prevent any liquid surfactants from interacting with the sodium bicarbonate acid reaction. Isolating the water (in the starch slurry composition) and the liquid surfactants (in the premix) before the final mix creates a better shelf life for the finished tablet.

Starch Slurry Composition Preparation Stage

As previously discussed, the starch slurry composition may include starch, isopropyl alcohol and water. In an embodiment, the starch may be present at about 30-50% by weight. In an embodiment, the alcohol may be present at about 20-50% by weight. In an embodiment, the water may be present at 20-50% by weight.

Table 2 below summarizes the above-described formula for the starch slurry composition. All percentages are by weight.

TABLE 2

Example Formula for Starch Slurry Composition

| INGREDIENT | % BY WEIGHT |
|---|---|
| Corn Starch | ~30-50% |
| Isopropyl Alcohol | ~20-50% |
| Water | ~20-50% |

The starch slurry composition can be made by mixing the listed ingredients at room temperature (about 60-90° F.), then heating to about 190 degrees F. to remove excess water using a wet granulation technique, with a mixing time of about 1 hour to ensure sufficient drying. Other suitable mixing procedures may also be used.

Premix Preparation Stage

As noted above, the second stage of effervescent tablet formulation may involve preparing a premix that includes the sodium carbonate, the glycol ether, and one or more of the surfactants of Table 1 that are sulfate-free. Table 3 shows three example premix formulas that may be used for producing effervescent tablets. All percentages are by weight.

TABLE 3

Example Premix Preparations for Effervescent Tablets

| INGREDIENT | % BY WEIGHT | | |
|---|---|---|---|
| | Premix 1 | Premix 2 | Premix 3 |
| Sodium Carbonate | 92.10% | 95.00% | 88.00% |
| Proteol ™ Oat PF Surfactant | 2.00% | 1.00% | 2.50% |
| Xiameter Surfactant | 1.30% | 1.00% | 1.50% |
| Glycol Ether EPh | 1.60% | 2.00% | 2.00% |
| Plantapon 611 L Surfactant | 3.00% | 1.00% | 6.00% |

Each premix example contains sodium carbonate, glycol ether, and three surfactants. The sodium carbonate (soda ash) used in each premix example is generic in nature and requires no further description. The glycol ether used in each premix example is Dowanol™ EPh (ethylene glycol phenyl ether), manufactured by Dow Chemical Company. The first-listed surfactant used in each premix is Proteol™ Oat PF, manufactured by SEPPIC, Inc. According to manufacturer specifications, the Proteol™ Oat PF product is a foaming anionic surfactant comprising sodium lauroyl oat amino acids. The second-listed surfactant used in each premix example is Xiameter®, manufactured by Dow Corning Company. According to manufacturer specifications, the Xiameter® product is a silicone emulsion formulated with nonionic, anionic, or cationic surfactants. The third-listed surfactant used in each premix example is Plantapon® 611 L, manufactured by BASF Company. According to manufacturer specifications, the Plantapon® 611 L product is an alkanolamide free, very mild, high active surfactant concentrate containing sodium laureth sulfate, lauryl glucoside, and cocamidopropyl betaine. Each of the above-listed surfactants is a liquid constituent, as is the glycol ether. The sodium carbonate is a powder constituent.

Each premix example can be made by mixing the listed ingredients at room temperature (about 60-90° F.) using a V-blender, with a mixing time of about 20 minutes to allow the liquid constituents to absorb across the powder constituent completely. Other suitable mixing equipment and procedures could also be used.

Final Mixing Stage

As previously noted, the third stage of effervescent tablet formulation may involve combining the starch slurry composition and the premix with the remaining ingredients of the final tablet composition. These ingredients include the sodium bicarbonate and the citric acid of Table 1, and may further include one or more additional surfactants of Table 1 that may either be sulfate-containing or sulfate-free.

Sulfate-Containing Effervescent Tablets

Table 4 shows three final tablet composition examples that may be used for producing sulfate-containing effervescent tablets. All percentages are by weight.

TABLE 4

Final Compositions for Sulfate-Containing Effervescent Tablets

| INGREDIENT | % BY WEIGHT | | |
|---|---|---|---|
| | Final Composition 1 Sulfate-Containing | Final Composition 2 Sulfate-Containing | Final Composition 3 Sulfate-Containing |
| Premix | 24.20% | 19% | 33% |
| Sodium Laurel Sulfate Surfactant | 2.00% | 4.00% | 2.00% |
| Sodium Sulfosuccinate Surfactant | 2.00% | 2.00% | 2.00% |
| Starch Slurry Composition | 39.00% | 45.00% | 35.00% |
| Sodium Bicarbonate | 10.00% | 10.00% | 10.00% |
| Citric Acid | 21.90% | 22.00% | 22.00% |

Each sulfate-containing effervescent tablet composition in Table 4 includes the starch slurry composition from Table 2 and one of the effervescent tablet premixes from Table 3. The additional ingredients are sodium laurel sulfate surfactant, sodium sulfosuccinate surfactant, sodium bicarbonate, and citric acid. Each of these ingredients is generic in nature and requires no further description.

Each final composition can be made by mixing the listed ingredients at room temperature (about 60-90° F.) using a V-blender, with a mixing time of about 20 minutes. Other suitable mixing equipment and procedures could also be used.

Sulfate-Free Effervescent Tablets

Table 5 shows four final composition examples that may be used for producing sulfate-free effervescent tablets. All percentages are by weight.

TABLE 5

Final Compositions for Sulfate-Free Effervescent Tablets

| | % BY WEIGHT | | | |
|---|---|---|---|---|
| INGREDIENT | Final Composition 4 Sulfate-Free | Final Composition 5 Sulfate-Free | Final Composition 6 Sulfate-Free | Final Composition 7 Sulfate-Free |
| Premix | 25.50% | 20.00% | 30% | 20% |
| Sodium Sulfosuccinate Surfactant | 2.00% | 2.00% | 2.00% | 2.00% |
| Sodium Cocoyl Isethionate Surfactant | 0.00% | 4.00% | 2.00% | 0.00% |
| N-Methyl Glycine Surfactant | 1.50% | 0.0% | 0.0% | 2.0% |
| Starch Slurry Composition | 39.00% | 42.00% | 35.00% | 44.00% |
| Sodium Bicarbonate | 10.00% | 10.00% | 10.00% | 10.00% |
| Citric Acid | 22.0% | 22.00% | 21.00% | 22.00% |

Each sulfate-free effervescent table formulation in Table 5 includes the starch slurry composition from Table 2 and one of the effervescent tablet premixes from Table 3. The additional ingredients are sodium sulfosuccinate surfactant, sodium cocoyl isethionate surfactant, n-methyl glycine surfactant, sodium bicarbonate, and citric acid. Each of these ingredients is generic in nature and requires no further description.

Each formulation can be made by mixing the listed ingredients at room temperature (about 60-90° F.) using a V-blender, with a mixing time of about 20 minutes. Other suitable mixing equipment and procedures could also be used.

Effervescent Tablet Formation and Testing

Each of the final effervescent tablet compositions of Table 4 and Table 5 was formed into tablets and tested. The tablets can be formed using a direct compression tablet press at about 5 tons of pressure. Other tablet forming techniques may also be used. Each tablet weighed about 1 gram. In order to test the dissolve time of the effervescent tablets, each test sample was immersed in room temperature water (about 60-90° F.) and the elapsed time was measured until the tablets were about 100% dissolved (without agitation). Each of the tested tablets was observed to dissolve in about 1 minute on average, with the shortest dissolve time being about 45 seconds and the longest dissolve time being about 1 min 28 seconds. The foaming and lathering characteristics of the tablets were also tested by way of hand washing with room temperature tap water, and subjectively compared. Final Composition 3 of Table 4, which had a dissolve time of about 1 minute, was observed to have the best foaming and lathering characteristics of the sulfate-containing tablets. Final Composition 6 of Table 5, which also had a dissolve time of about 1 minute, was observed to have the best foaming and lathering characteristics of the sulfate-free tablets.

Non-Effervescent Tablet Preparation

In an embodiment, the following example formula may be used to produce a personal care cleaning composition that can be formed into non-effervescent cleaning tablets:
  (a) Starch slurry composition at about 70-95% by weight, with about 90% by weight being preferred; and
  (b) Sodium cocoyl isethionate surfactant at about 5-30% by weight, with about 10% by weight being preferred.

Table 6 below summarizes the above-described formula for non-effervescent tablets. All percentages are by weight.

TABLE 6

Example Formula for Non-effervescent Tablets

| | % BY WEIGHT | |
|---|---|---|
| INGREDIENT | BROAD RANGE | PREFERRED RANGE |
| Starch Slurry Composition | ~70.00-95.00% | ~90% |
| Sodium Cocoyl Isethionate Surfactant | ~5.00-30.00% | ~10% |

Non-effervescent tablet compositions can be made using a two-stage process. A first stage may involve preparing a starch slurry composition in accordance with Table 2, as previously described. A second stage may involve mixing the starch slurry composition with the sodium cocoyl isethionate surfactant, e.g., using a V-blender with a suitable mixing time (e.g., about 20 minutes). The tablets may then be pressed using the same procedure used for the effervescent tablets.

Note that the non-effervescent tablets did not require glycol ether for binding because there was no interference from an effervescent reaction. The starch slurry mix acts as both a binder and an excipient.

In order to test the dissolve time of the non-effervescent tablets, a number of tablet samples were made using a tablet composition having the weight percentages shown in table 7.

TABLE 7

Non-Effervescent tablets

| INGREDIENT | % BY WEIGHT |
|---|---|
| Starch Slurry Composition | 90.00% |
| Sodium Cocoyl Isethionate Surfactant | 10.00% |

The non-effervescent tablets can be formed using a direct compression tablet press at 5 tons of pressure. Other suitable tablet forming techniques may also be used. Each tablet weighed about 1 gram. The tablets were tested by using a hand-washing protocol in which the tablets were rubbed between the tester's hands under a running faucet providing a continuous cascade of room temperature water (about 60-90° F.). Each tablet was observed to dissolve about 100% almost instantaneously (e.g., within about 1-3 seconds) while exhibiting good foaming and lathering action.

Personal Care Cleaning Tablets with Antimicrobial Action

Experiments were performed to determine whether personal care cleaning tablets as disclosed herein could be enhanced to provide antimicrobial action. Non-effervescent tablets as discussed in connection with Table 7 were selected for these experiments. One way that the antimicrobial agent may be introduced is by way of a modified starch slurry composition as shown in Table 8 below.

TABLE 8

Example Formula for Antimicrobial Starch Slurry Composition

| INGREDIENT | % BY WEIGHT |
| --- | --- |
| Corn Starch | 50% |
| Isopropyl Alcohol | 15% |
| Water | 20% |
| Antimicrobial Agent | 15% |

The antimicrobial agent selected for testing was Dermosoft® 1388 eco from Evonik Dr. Straetmans GmbH. According to manufacturer specifications, the Dermosoft® 1388 eco product contains glycerin, water, sodium levulinate and sodium anisate. Other antimicrobial agents could also be used. The final tablet composition was as shown in Table 7 above. In order to ensure good antimicrobial efficacy, the final composition may be adjusted as necessary to a ph range of about 5-6 (e.g., by adding citric acid).

Luminometer testing was performed to compare the antimicrobial action of tablets produced according to Table 7 using the antimicrobial starch slurry composition (AMSC) of Table 8 versus tablets produced according to Table 7 using a starch slurry composition per Table 2 with no antimicrobial agent (non-AMSC). The results are shown in Table 9 below.

TABLE 9

Luminometer Test Results

| | RLU OUTPUT | | |
| --- | --- | --- | --- |
| TEST SUBJECT | RLU - Pre-Washing | RLU-Non-AMSC | RLU-AMSC |
| Subject 1 | 45577 | | 233 |
| Subject 2 | 5966 | 3127 | 187 |
| Subject 3 | 44593 | 3074 | 0 |

Three test subjects were used. Each subject was swabbed and tested prior to hand washing and then following hand washing using either a non-AMSC tablet, an AMSC tablet, or both. The luminometer was a Novalum II ATP Detection System from Charm Sciences Inc. All results were measured as Relative Light Unit (RLU) output. Test subject 1 had an initial RLU reading of 45577 prior to hand washing. After washing with an AMSC tablet, the RLU reading was 233. Test subject 1 did not wash with a non-AMSC tablet. Test subject 2 had an initial RLU reading of 5966 prior to hand washing. After washing with a non-AMSC tablet, the RLU reading was 3127. After further washing with an AMSC tablet, the RLU reading was 187. Test subject 3 had an initial RLU reading of 44593 prior to hand washing. After washing with a non-AMSC tablet, the RLU reading was 3074. After further washing with an AMSC tablet, the RLU reading was 0.

The foregoing data demonstrate that the AMSC tablets dramatically reduced microbial activity during hand washing as compared to non-AMSC tablets. It will be appreciated that although only non-effervescent AMSC tablets were tested, similar antimicrobial action may be obtained with effervescent AMSC tablets.

Accordingly, a personal care cleaning composition in tablet form, together with a manufacturing method therefore, have been disclosed. Although various embodiments have been described, it should be apparent that many variations and alternative embodiments could be implemented in accordance with the inventive concepts disclosed herein. For example, it was previously noted that the tablet formulas disclosed herein can be adjusted to work as a hand wash, a face wash, a body wash, or a hair wash. This may be accomplished by changing the surfactants present in the tablet composition using known techniques. It will therefore be understood that the invention is not to be in any way limited except in accordance with the spirit of the appended claims and their equivalents.

What is claimed is:

1. A personal care cleaning composition in tablet form, comprising:
   a surfactant;
   a starch composition comprising starch, alcohol and water; and
   wherein said starch composition is formed from a starch slurry comprising corn starch in a range of about 30-50% by weight, isopropyl alcohol in a range of about 20-50% by weight, and water in a range of about 20-50% by weight.

2. The personal care cleaning composition of claim 1, wherein said surfactant comprises more than one surfactants.

3. The personal care cleaning composition of claim 2, wherein said more than one surfactants are selected from the group consisting of non-ionic surfactants, anionic surfactants, cationic surfactants, zwitterionic surfactants, and combinations thereof.

4. The personal care cleaning composition of claim 2, wherein said more than one surfactants are selected from the group consisting of liquid surfactants and powder surfactants.

5. The personal care cleaning composition of claim 2, wherein said more than one surfactants are selected from the group consisting of sulfate-containing surfactants and sulfate-free surfactants.

6. The personal care cleaning composition of claim 1 wherein said surfactant is present in a range of about 5-30% by weight and said starch composition is present in a range of about 70-95% by weight.

7. The personal care cleaning composition of claim 1, wherein said composition comprises an antimicrobial agent.

8. The personal care cleaning composition of claim 1, further including:
   sodium carbonate;
   sodium bicarbonate;
   citric acid; and
   glycol ether.

9. The personal care cleaning composition of claim 8, wherein said surfactant comprises more than one surfactants.

10. The personal care cleaning composition of claim 9, wherein said more than one surfactants are selected from the group consisting of non-ionic surfactants, anionic surfactants, cationic surfactants, zwitterionic surfactants, and combinations thereof.

11. The personal care cleaning composition of claim 9, wherein said more than one surfactants are selected from the group consisting of liquid surfactants, powder surfactants, sulfate-containing surfactants and sulfate-free surfactants.

12. The personal care cleaning composition of claim 8, wherein said glycol ether is selected from the group consisting of ethylene oxide glycol ethers and propylene oxide glycol ethers.

13. The personal care cleaning composition of claim 8, wherein said glycol ether is selected from the group consisting of ethylene glycol phenyl ether, ethylene glycol butyl ether, dipropylene glycol n-butyl ether, dipropylene glycol methyl ether, tripopylene glycol methyl ether, and polyethylene glycol 800 MW or higher.

14. The personal care cleaning composition of claim 8, wherein said surfactant is present in a range of about 1-10% by weight, said starch composition is present in a range of about 1-50% by weight, said sodium carbonate is present in a range of about 1-30% by weight, said sodium bicarbonate is present in a range of about 1-20% by weight, said citric acid is present in a range of about 1-30% by weight, and said glycol ether is present in a range of about 0.25-0.75% by weight.

15. The personal care cleaning composition of claim 8, wherein said composition comprises an antimicrobial agent.

16. A method of manufacturing a personal care cleaning composition in tablet form, comprising:
preparing a starch slurry composition comprising starch, alcohol and water;
said starch slurry composition comprising corn starch in a range of about 30-50% by weight, isopropyl alcohol in a range of about 20-50% by weight, and water in a range of about 20-50% by weight;
preparing a mixture of said starch slurry composition and a surfactant; and
pressing said mixture into a tablet.

17. The method of claim 16, wherein said surfactant comprises more than one surfactants.

18. The method of claim 17, wherein said more than one surfactants are selected from the group consisting of non-ionic surfactants, anionic surfactants, cationic surfactants, zwitterionic surfactants, and combinations thereof.

19. The method of claim 17, wherein said more than one surfactants are selected from the group consisting of liquid surfactants and powder surfactants.

20. The method of claim 17, wherein said more than one surfactants include sulfate-containing surfactants and sulfate-free surfactants.

21. The method of claim 16, wherein said surfactant is present in a range of about 5-30% by weight and said starch composition is present in a range of about 70-95% by weight.

22. The method of claim 16, further including adding an antimicrobial agent to said mixture.

23. The method of claim 16, further including adding sodium carbonate, sodium bicarbonate, citric acid and glycol ether to said mixture.

24. The method of claim 23, wherein said surfactant comprises more than one surfactants.

25. The method of claim 24, wherein said more than one surfactants are selected from the group consisting of non-ionic surfactants, anionic surfactants, cationic surfactants, zwitterionic surfactants, and combinations thereof.

26. The method of claim 24, wherein said more than one surfactants are selected from the group consisting of liquid surfactants, powder surfactants, sulfate-containing surfactants and sulfate-free surfactants.

27. The method of claim 23, wherein said glycol ether is selected from the group consisting of ethylene oxide glycol ethers and propylene oxide glycol ethers.

28. The method of claim 23, wherein said glycol ether is selected from the group consisting of ethylene glycol phenyl ether, ethylene glycol butyl ether, dipropylene glycol n-butyl ether, dipropylene glycol methel ether, tripopylene glycol methyl ether, and polyethylene glycol 800 MW or higher.

29. The method of claim 23, wherein said surfactant is present in a range of about 1-10% by weight, said starch slurry composition is present in a range of about 1-50% by weight, said sodium carbonate is present in a range of about 1-30% by weight, said sodium bicarbonate is present in a range of about 1-20% by weight, said citric acid is present in a range of about 1-30% by weight, and said glycol ether is present in a range of about 0.25-0.75% by weight.

30. The method of claim 23, further including adding an antimicrobial agent to said mixture.

* * * * *